United States Patent
Simmons et al.

(10) Patent No.: US 7,628,767 B1
(45) Date of Patent: Dec. 8, 2009

(54) METHOD FOR PREVENTING INFECTION AND MAINTAINING ASEPTIC EPIDERMAL AREAS USING A REUSABLE NON-DEFORMING FLEXIBLE PROTECTIVE COVER

(76) Inventors: Kathy A. Simmons, 25323 Intrepid La., Galveston, TX (US) 77554; Mary E. Simmons, 25323 Intrepid La., Galveston, TX (US) 77554

( * ) Notice: Subject to any disclaimer, the term of this patent is extended or adjusted under 35 U.S.C. 154(b) by 0 days.

(21) Appl. No.: 11/857,022

(22) Filed: Sep. 18, 2007

(51) Int. Cl.
*A61F 13/00* (2006.01)
*A61F 5/00* (2006.01)
*A61F 5/44* (2006.01)

(52) U.S. Cl. ............... 602/79; 602/41; 602/42; 602/43; 602/44; 602/78; 602/3; 128/888; 128/889; 128/849; 128/850; 128/851; 128/852; 128/853; 128/893; 128/894; 128/96.1; 128/99.1; 128/100.1; 128/105.1; 604/304; 604/305; 604/306; 604/307; 604/308; 604/309; 604/310; 604/311; 604/312; 604/313; 604/338; 604/353; 604/355; 604/164.08; 604/192; 604/263; 604/327; 604/332; 604/337; 206/438; 206/440; 2/908; D24/190; D24/189; 24/572.1

(58) Field of Classification Search ............. 602/41–44, 602/79, 78, 3; 604/46, 192, 289, 304–316, 604/164.08, 263, 327, 332, 337–338, 353, 604/355, 303, 179–180, 174; 128/888–889, 128/849–853, 893–894, 96.1, 99.1, 100.1, 128/105.1; 206/438, 440; 2/908; D24/190, D24/189; 24/572.1
See application file for complete search history.

(56) References Cited

U.S. PATENT DOCUMENTS

| | | | | |
|---|---|---|---|---|
| 2,367,690 A | * | 1/1945 | Purdy | 128/888 |
| 3,234,941 A | * | 2/1966 | Tucker | 128/888 |
| 3,520,306 A | * | 7/1970 | Gardner et al. | 606/215 |
| 6,987,209 B2 | * | 1/2006 | Augustine et al. | 602/42 |
| 2001/0029956 A1 | * | 10/2001 | Argenta et al. | 128/897 |
| 2003/0120194 A1 | * | 6/2003 | Stapf | 602/48 |
| 2003/0139696 A1 | * | 7/2003 | Boukanov et al. | 602/41 |

FOREIGN PATENT DOCUMENTS

JP     2000116691 A   *  4/2000

OTHER PUBLICATIONS

English Translation of JP 2000116691.*

* cited by examiner

*Primary Examiner*—Patricia M Bianco
*Assistant Examiner*—Tarla R Patel
(74) *Attorney, Agent, or Firm*—Buskop Law Group, PC; Wendy Buskop (57) ABSTRACT

A method for preventing infection and maintaining aseptic epidermal areas by preventing contaminated fluid from entering an open epidermal site on a user, comprising the steps of: removably attaching at least one adjustable strap to a reusable non-deforming flexible protective cover comprising a sealing member, covering the open epidermal site with the reusable non-deforming flexible protective cover while maintaining a space between the reusable non-deforming flexible protective cover and the open epidermal site, and tightening the at least one adjustable strap to secure the reusable non-deforming flexible protective cove over the open epidermal site to create a fluid-tight seal between the sealing member and the open epidermal site, thereby preventing contaminated fluid from entering the open epidermal site.

10 Claims, 7 Drawing Sheets

METHOD FOR PREVENTING INFECTION AND MAINTAINING ASEPTIC EPIDERMAL AREAS USING A REUSABLE NON-DEFORMING FLEXIBLE PROTECTIVE COVER

FIELD

The present embodiments relate to a method for preventing infection and maintaining aseptic epidermal areas through use of a reusable, non-deforming flexible protective cover for preventing contaminated fluid from entering an open epidermal site on a user.

BACKGROUND

A need exists for a method for protecting an open epidermal site that can form a water-tight seal to effectively prevent fluid from entering the open epidermal site. A need exists for a method for preventing infection that incorporates use of a reusable, non-deformable protective cover having sufficient strength or reinforcement means for maintaining a seal and means for preventing contact with an open epidermal site when touched or impacted by light or moderate pressure.

A need exists for a method for preventing infection and maintaining sterile epidermal areas that can be used on any part of a human or animal body.

The present embodiments meet these needs.

BRIEF DESCRIPTION OF THE DRAWINGS

The detailed description will be better understood in conjunction with the accompanying drawings as follows.

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways.

The present embodiments relate to a method for preventing infection and maintaining aseptic epidermal areas using a reusable, non-deformable flexible protective cover for preventing contaminated fluid from entering an open epidermal site.

The present method incorporates the use of a reusable, non-deforming flexible protective cover that advantageously provides the dual benefits of both physically protecting an open epidermal site from contact, and forming a water-tight seal for preventing fluid from entering the open epidermal site.

The protection of an open epidermal site, such as a surgical site, a catheter entry or exit site, or the site of an intravenous line, can be accomplished by physically covering the open epidermal site while maintaining a space between the flexible protective cover and the open epidermal site, thereby preventing pain, irritation, injury, and infection that can be caused through accidental contact. The flexible protective cover used to cover the open epidermal site can be made from a sturdy material and can have reinforcement means, such as interior ribs and spacers, to prevent the flexible protective cover from deforming under light or moderate pressure caused by contact.

The prevention of fluid entry into an open epidermal site can be accomplished using a sealing member that provides a sealing engagement between the flexible protective cover and the open epidermal site. The sealing engagement allows a human or animal with a wound or similar open epidermal site to bathe or shower normally, and to withstand exposure to rain and other precipitation without allowing the entry of contaminated fluid into the open epidermal site. The prevention of fluid from entering an open epidermal site can prevent pain, irritation, injury, infection, and can prevent a wound dressing, such as Tegaderm™, from becoming wet, necessitating frequent dressing changes. Further, the ability to bathe and shower normally allows an individual to maintain proper hygiene and morale, to avoid further illnesses or infections caused by improper hygiene, or possible contamination of sterile environments, such as hospitals, caused by improper hygiene.

Use of a flexible protective cover, which can be advantageously made from a flexible material, such as a silicone-based material, provides flexibility which allows open epidermal sites on any part of a human or animal body to be effectively covered and sealed to prevent fluid entry. Further, the flexible material can be a non-irritating, non-toxic, hypoallergenic, recyclable material, thereby allowing any individual, including individuals with allergies or sensitivities to certain materials, to wear the flexible protective cover without experiencing irritation or allergic reaction.

Unlike other dressing, sealing, or covering means for an open epidermal site, the flexible protective cover used by the present method is reusable, able to be removed and reapplied to a user multiple times, or aseptically cleaned and used to cover open epidermal sites on other users.

The flexible protective cover can additionally have any shape, including shapes suitable for promoting entertainment, comfort, education, or proper hygienic behaviors among children, such as shapes of cartoon characters. The shape can also be functional, to allow protection of uniquely shaped open epidermal sites, or open epidermal sites on locations of the body that are otherwise difficult to protect.

The present method can further advantageously include removably attaching one or more adjustable securing means, such as straps with fasteners, to the flexible protective cover, allowing the flexible protective cover to be worn by humans or animals of any size or to be secured to body parts of any size.

Further, the present method can also include engaging and securing tubing or other medical equipment, such as intravenous lines or catheters, in an opening in the flexible protective cover, such as a slit within an interior spacer and an opening within an edge. This securing can prevent irritation and injury caused by motion of the medical equipment, and can also prevent damage or malfunction of the medical equipment, such as kinks or leaks in a line or tube, caused by movement or contact with the medical equipment.

The present method is advantageously simple to perform, using lightweight equipment that is easy to operate, allowing children, elderly individuals, persons with disabilities, persons recovering from surgical procedures, and persons having illnesses, injuries, or one or more open epidermal sites, to protect an open epidermal site from contaminated fluid with minimal or no assistance. The present method can incorporate use of elastic adjustable straps, buckles or slidable fasteners having quick-release features, and a lightweight flexible protective cover that is easy to position and adjust, requiring only pressure from adjustable straps to form a fluid-tight seal.

The present method includes the step of removably attaching one or more adjustable straps to a reusable, non-deforming flexible protective cover.

The adjustable straps can have any length, such as about two inches to about six inches for securing around the wrist of a child, or ten feet or more to secure around the midsection of a horse. The adjustable straps can have any width, ranging from about 0.5 inches to about 4 inches or more.

The adjustable straps can be made from webbed materials, textiles, hypoallergenic materials, elastic materials, such as Stretchrite Polyester Non-Roll WaistBand Elastic made by Dyno Merchandise of Pompano Beach, Fla., or combinations thereof. The adjustable straps can include buckles, slidable fasteners, or other similar fastening or tightening means for enabling the adjustable straps to be cinched to a user. It is contemplated that the buckles can include plastic or metal buckles having snapping or locking means with a quick release feature, pegs and holes, and other types of buckles or tightening means.

In an embodiment, one or more fasteners can be removably or non-removably adhered to the reusable, non-deforming flexible protective cover. The fasteners and means for engaging the fasteners can include loops and hooks of a hook and loop fastening material, such as Velcro™. Two-part fasteners, such as Velcro™, can include use of an anchored portion adhered to the reusable, non-deforming flexible protective cover, and a second portion adhered to the one or more adjustable straps. Use of other similar fastening means, such as reusable adhesives, snaps, or loops of plastic or another material molded to the central portion, is also contemplated.

The adjustable straps and fasteners can have varying configurations to enhance ease of use and the strength of the fluid tight seal. In an embodiment, at least two adjustable straps can engage a first fastening strap and a second fastening strap, which provide pressure to the outside surface of the flexible protective cover to create a fluid-tight seal. The fastening straps engage the fasteners disposed on the flexible protective cover while the adjustable straps secure the cover body to the user.

The present method can also include covering an open epidermal site, which can include a dressing, a catheter, an intravenous medical line, a surgical incision site, an intravenous line point of entry, a peripheral intravenous line point of entry, a port for central venous access, a central venous line point of entry, a catheter line point of entry, a boil, a blister, a wound, one or more sutures, or combinations thereof, with the reusable, non-deforming flexible protective cover.

The present method can be used to protect open epidermal sites on any creature, including a human, a horse, a cow, or a similar domestic animal.

The reusable, non-deforming flexible protective cover can have numerous shapes and configurations depending on the location, size, and shape of the open epidermal site and the preferences of the user.

The reusable, non-deforming flexible protective cover can have a one-piece flexible cover body, which can be rectangular, such as a rectangular body ranging from about two inches to about twelve inches in length, about one inch to about eight inches in width, and about 0.5 inches to about six inches in height. For example, the one-piece flexible cover body could have a length of twelve inches and a width of two inches to cover a long surgical incision in an abdomen, or a length of twelve inches and a width of eight inches to cover a twelve inch by eight inch wound dressing. The height of the one-piece flexible cover body can vary to accommodate pieces of medical equipment, such as catheters, or thick dressings, such as bandages having a thickness of four inches or more.

It is also contemplated that the one-piece flexible cover body can be round, such as a circle having a diameter ranging from about two inches to about twelve inches, or an elliptical shape having a length of about two inches and a width of about 1.5 inches for covering an eye after surgery. Round-shaped one-piece flexible cover bodies can also include oblong shapes, oval shapes, elliptical shapes, or other rounded shapes, such as polygons with rounded corners.

In an embodiment, the one-piece flexible cover body can have a cartoon shape, such as "Spongebob Squarepants"™ for providing enjoyment and comfort to child-aged users. "Cartoon-shaped" one-piece flexible cover bodies can include the shape of any article, including plants, animals, sport symbols, logos, equipment, cartoon characters, famous persons, polygons, other similar shapes, parts thereof, and combinations thereof.

The one-piece cover body can also have an irregular shape to facilitate covering an irregularly shaped open epidermal site, or an open epidermal site on a location on a body that is difficult to protect.

The one-piece flexible cover body can be made from a non-irritating, non-toxic, hypoallergenic, recyclable, silicone based material, such as innocuity silica gel. Use of innocuity polyvinylchloride is also contemplated. It is contemplated that the material of the one-piece flexible cover body can have a rigidity of 90 degrees. The material can be white, or the material can be provided with one or more colors. It is also contemplated that the one-piece flexible cover body can be decorated, such as by applying one or more adhesive decorations, paints, molds adhered to the outside surface, or similar materials.

The one-piece flexible cover body can include an edge made from a bendable, shapeable material, such as a 24" Flexible Curve made by the C-Thru® Ruler Company of Bloomfield, Conn., to allow the flexible protective cover to be provided with any shape, as needed, to cover an open epidermal site having an irregular shape, or an open epidermal site on a location on a body that is difficult to protect. The shapeable material is non-brittle, is generally stiff, and provides horizontal shaping, as opposed to vertical shaping. It is preferred that the shape of the material is bidirectional on a X-axis without being deformable along a Y-axis. The shapeable material can have a thickness ranging from about 0.25 inches to about 1 inch. The shapeable material, in an embodiment, can have a core that is encapsulated with a softer thermoplastic or blend of thermoplastic with elastomer.

In yet another embodiment, the core of the shapeable material could be encapsulated with a sealing material, enabling the shapeable bendable material to provide the dual functionality of forming a shape and seal without the need for a two-layer structure, or for the use of adhesives, which can cause allergic reactions in certain users.

It is contemplated that the one-piece flexible cover body can include a central portion connected substantially perpendicular to an edge. The central portion can have a thickness ranging from about 0.125 inches to about 0.5 inches, as needed to provide strength and stability to protect an open epidermal site from contact. In an embodiment, the central portion can made from a very thin material, such as a flexible plastic barrier.

One or more ribs can extend along the inside surface of the central portion for preventing deformation of the central portion, such as deformation caused by accidental contact or impact. Any number of ribs can be used to reinforce the central portion, such as two parallel ribs integrally molded to the inside surface of the central portion that have a length equal to a dimension of the central portion, a width ranging from about 0.5 inches to about 2 inches, and a thickness ranging from about 0.125 inches to about 0.5 inches. In a contemplated embodiment, from one to six ribs can be integrally molded to the inside surface of the central portion. It is also contemplated that the ribs can be made from a different material than the central body, such as a stiff plastic, to provide added strength and resistance to deformation.

In an embodiment, the central portion can also include one or more spacers integral with the inside surface of the central portion and horizontal to one or more of the ribs, which can provide additional reinforcement for preventing deformation of the central portion. It is contemplated that a spacer can have a depth slightly larger than that of the ribs, and any width, such as 0.125 inches. It is contemplated that up to four spacers can be integral with the inside surface, depending on the size of the one-piece flexible cover body. Each spacer can also include a slit for securely engaging tubing or other medical equipment connected to the open epidermal site. The slit can have a width ranging from about 0.125 inches to about 1 inch. It is contemplated that the width or diameter of the slit can be slightly smaller than the diameter of the tubing to ensure a secure, fluid-tight fit.

In an embodiment, a rectangular one-piece flexible cover body can include a top edge, a first side edge, and a second side edge, each secured substantially perpendicular to the central portion. A angular edge can be secured to the central portion at an angle, which can range from ten degrees to ninety degrees. Each edge can have a thickness ranging from about 0.125 inches to about 0.5 inches, or thicker if additional thickness is needed to provide strength and stability to the one-piece flexible cover body. It is contemplated that each edge can have a depth ranging from about 0.5 inches to about 4 inches, as needed to accommodate thick dressings or bandages. In an embodiment, the angular edge can include an opening, such as a slit, a cut, a hole, or a similar aperture having a diameter ranging from about 0.125 inches to about 1 inch, for securely engaging, in a force fit, tubing or other medical equipment connected to the open epidermal site. It is contemplated that the diameter of the opening can be slightly smaller than the diameter of the tubing to ensure a secure, fluid-tight fit.

A round one-piece flexible cover body can have a single edge encircling the central portion and connected substantially perpendicular to the central portion. One-piece flexible cover bodies having other shapes, such as cartoon shapes, can have similar edge configurations, encircling the perimeter of the central portion and connected substantially perpendicular to the central portion, or at an angle to the central portion. The edges can include one or more openings, as described previously, for securely engaging tubing or other medical equipment.

In an embodiment, the opening can be defined by a groove, an outline, or a perforated section of the edge that can be selectively cut to create the opening.

A lip can be disposed around each of the edges. The lip can have a width slightly wider than that of the edges. The lip can include a sealing member for providing a sealing engagement between the lip and the open epidermal site. The sealing engagement is contemplated to be water-tight, able to prevent fluid from entering the open epidermal site.

The sealing member can include a deformation resistant tubing, that can reassume its shape after light compression. The deformation resistant tubing can be made from flexible, compressible plastic or silicone, or other non-latex materials, having an inner diameter of up to three inches.

It is further contemplated that the sealing member can include inflatable tubing, such as a Pre-Inflated Cuff™ made by Laerdal or a Pocket Mask Seal made by Ambu™, having one or more valves used to inflate the tubing after compression. The inflation of the tubing can seal gaps between the central portion and the open epidermal site. In an embodiment, the one or more valves can be removable valves that are removed after inflation.

It is further contemplated that the present method can include the step of inflating an inflatable sealing member to seal gaps between the reusable, non-deforming flexible protective cover and the open epidermal site.

It is also contemplated that the flexible protective cover can include a one-piece flexible cover body having any shape and corresponding edges, as described previously, however, in lieu of a lip encircling the edges, the flexible protective cover can include an inflatable sealing member integral with each of the edges providing a sealing engagement between the central portion and the open epidermal site.

The present method includes tightening the one or more adjustable straps to secure the reusable, non-deforming flexible protective cover over the open epidermal site. This securing creates a fluid-tight seal between the sealing member and the open epidermal site, thereby preventing contaminated fluid from entering the open epidermal site.

Tightening of the adjustable straps can be performed using one or more buckles, clasps, loops, or slidable fasteners that engage the adjustable straps. It is also contemplated that the straps can be made from an elastic material that conforms to a user's body without the need of tightening means.

In an embodiment, the present method can include the step of applying one or more dressings, such as bandages, gauze, or sutures, or one or more pieces of medical equipment, such as intravenous lines, central lines, Port-A-Caths™, or catheters, to the open epidermal site. It is contemplated that a user of the present method can apply and change dressings as frequently as required, reusing the reusable, non-deformable flexible protective cover to create a fluid-tight seal for bathing, showering, possibly swimming, or traveling through areas with precipitation. The present method can also be used to protect an open epidermal site that lacks a dressing or any other medical equipment.

In a contemplated embodiment, the present method can also include the step of securely engaging tubing connected to the open epidermal site with at least one opening in the reusable, non-deforming flexible protective cover. The opening can include a slit, a cut, a hole, or a similar aperture disposed through an edge of the reusable, non-deforming flexible protective cover. Openings disposed through one or more interior spacers within the reusable, non-deforming flexible protective cover are also contemplated. The diameter of each opening can be slightly smaller than the diameter of the tubing to ensure a secure, fluid-tight fit.

The present method can further include the step of cinching the reusable, non-deforming flexible protective cover to the user to prevent accidental loosening or movement of the flexible protective cover.

It is further contemplated that the present method can include the step of aseptically cleaning the flexible protective cover, which can be performed by wiping the reusable, non-deforming flexible protective cover with an aseptic cleaner, such as an alcohol, Lysol™, or Hibiclens™.

Figure 1:
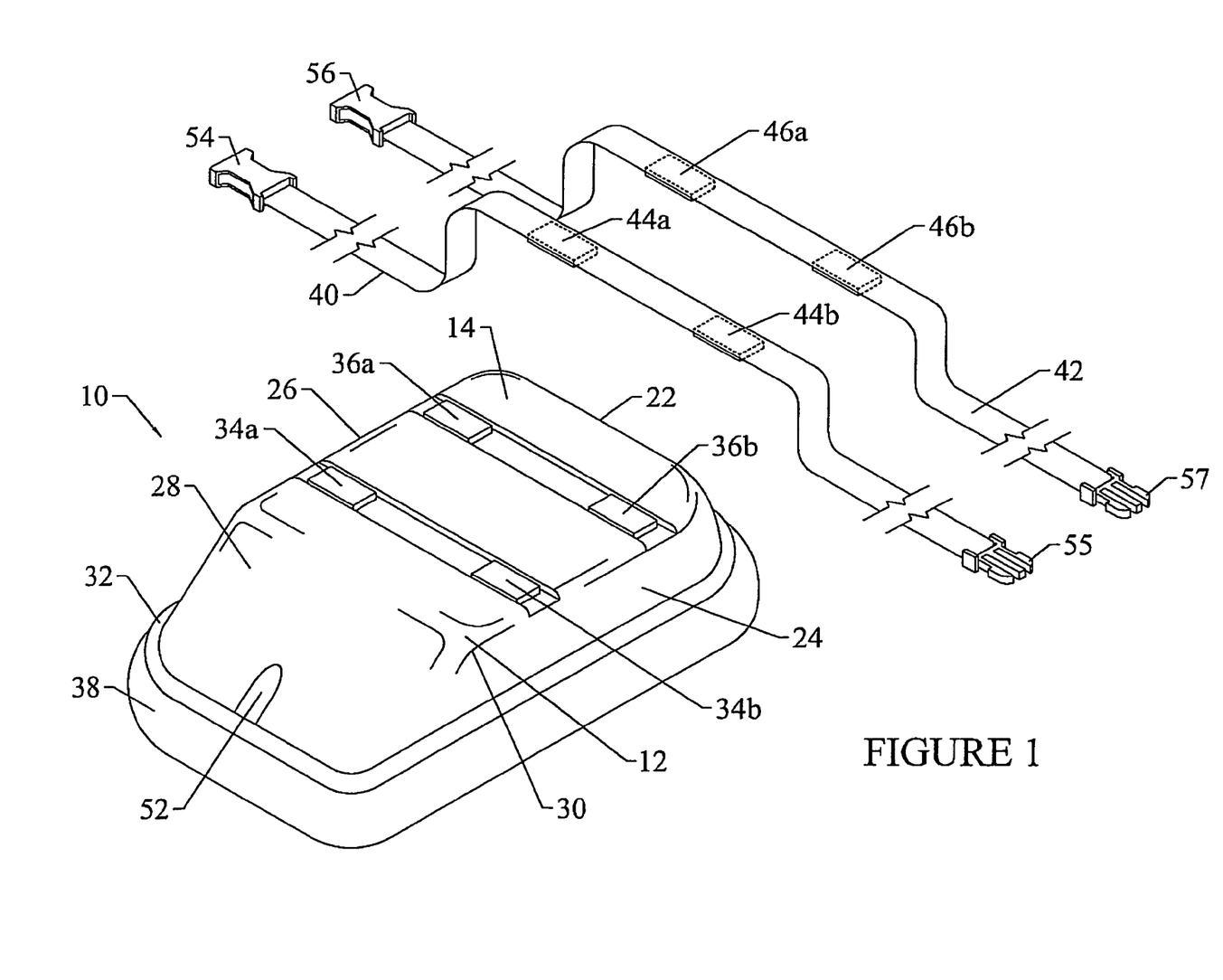
FIG. 1 depicts a perspective view of the outside surface of an embodiment of the present flexible protective cover.

Referring now to the Figures, FIG. 1 is a perspective view of an outside surface (14) of an embodiment of a flexible protective cover useable with the present method is shown.

FIG. 1 depicts a one-piece flexible cover body (10) with a central portion (12) having outside surface (14). Central portion (12) is connected substantially perpendicular to a top edge (22), a first side edge (24), and a second side edge (26). Central portion (12) is connected at an angle (30) to an angular edge (28). Angle (30) can be any angle, including angles ranging from ten degrees to ninety degrees. Thus, in an embodiment, angular edge (28) can also be connected substantially perpendicular to central portion (12).

A lip (32) is disposed around top edge (22), first side edge (24), second side edge (26), and angular edge (28), for engaging a sealing member (38). While FIG. 1 depicts sealing member (38) as deformation resistant tubing, other sealing members such as plastic-coated metal, inflatable tubing, and similar plastic, rubber, polymer, or other materials able to form a fluid-tight seal on a user are also contemplated.

Angular edge (28) is depicted having an opening (52) for securely engaging tubing or similar medical equipment connected to an open epidermal site beneath one-piece flexible cover body (10).

Outside surface (14) is depicted having a first anchored portion (34a) and a second anchored portion (34b) of a first fastener, and a first anchored portion (36a) and a second anchored portion (36b) of a second fastener. While FIG. 1 depicts a first and second fastener each having two anchored portions, any number of fasteners having any number of anchored portions can be used. Use of other fastening means lacking anchored portions is also contemplated. In an embodiment, use of fasteners can be omitted.

A first adjustable strap (40) and a second adjustable strap (42) are shown disengaged from one-piece flexible cover body (10). First adjustable strap (40) has a first means (44a) for engaging first anchored portion (34a) of the first fastener. First adjustable strap (40) also has a second means (44b) for engaging second anchored portion (34b) of the first fastener. Second adjustable strap (42) has a first means (46a) for engaging first anchored portion (36a) of the second fastener. Second adjustable strap (42) also has a second means (46b) for engaging second anchored portion (36b) of the second fastener.

While first adjustable strap (40) and second adjustable strap (42) are depicted each having two means for engaging two anchored portions of two fasteners, any number of fasteners or other removable fastening means can be used. It is also contemplated that first adjustable strap (40) and second adjustable strap (42) can be tightened over one-piece flexible cover body (10) without the use of fasteners.

First adjustable strap (40) has a first buckle (54) and a means for engaging first buckle (55), which can include any type of locking means with a quick release mechanism, pegs and holes, or other similar engagement means. Second adjustable strap (42) has a second buckle (56) and a means for engaging second buckle (57). Second buckle (56) can be of similar or different construction and design as first buckle (54).

Figure 2:
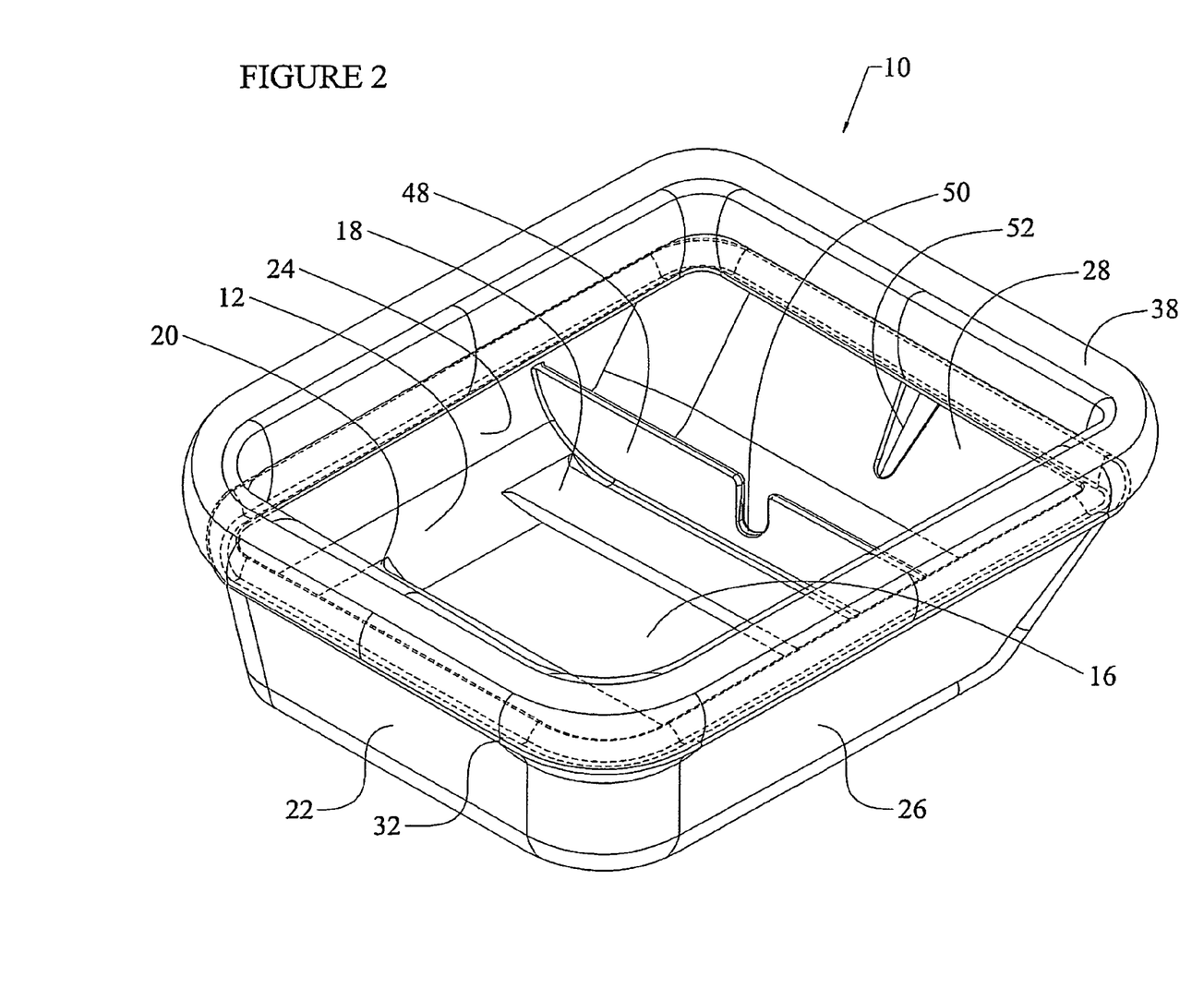
FIG. 2 depicts a perspective view of the inside surface of the flexible protective cover of FIG. 1.

FIG. 2 is a perspective view of an inside surface (16) of the flexible protective cover depicted in FIG. 1. FIG. 2 further depicts the embodied flexible protective cover having one-piece flexible cover body (10) with central portion (12) having inside surface (16). Central portion (12) is connected to top edge (22), first side edge (24), second side edge (26), and angular edge (28). Angular edge (28) has opening (52) for securely engaging tubing or other medical equipment connected to an open epidermal site underneath one-piece flexible cover body (10).

Lip (32) is disposed on each of top edge (22), first side edge (24), second side edge (26), and angular edge (28). Sealing member (38) is shown disposed on lip (32) for creating a sealing engagement over an open epidermal site.

Inside surface (16) is shown having a first rib (18) and a second rib (20) for preventing deformation of one-piece flexible cover body (10). While FIG. 2 depicts two parallel ribs extending parallel to top edge (22), inside surface (16) can have any number of ribs that can be parallel, perpendicular, round, or shaped, and can extend wholly or partially across any dimension of one-piece flexible cover body (10).

A spacer (48) is also shown disposed on inside surface (16), for providing additional strength and resistance to deformation. Spacer (48) has a slit (50) for receiving tubing or medical equipment connected to an open epidermal site underneath one-piece flexible cover body (10). While FIG. 2 depicts one spacer (48), parallel to top edge (22) any number of spacers having any arrangement can be disposed on inside surface (16). It is also contemplated that spacer (48) can be omitted to provide additional space for very long, wide, or thick dressings or bandages, or when the additional strength and resistance provided by spacer (48) is not required.

Figure 3:
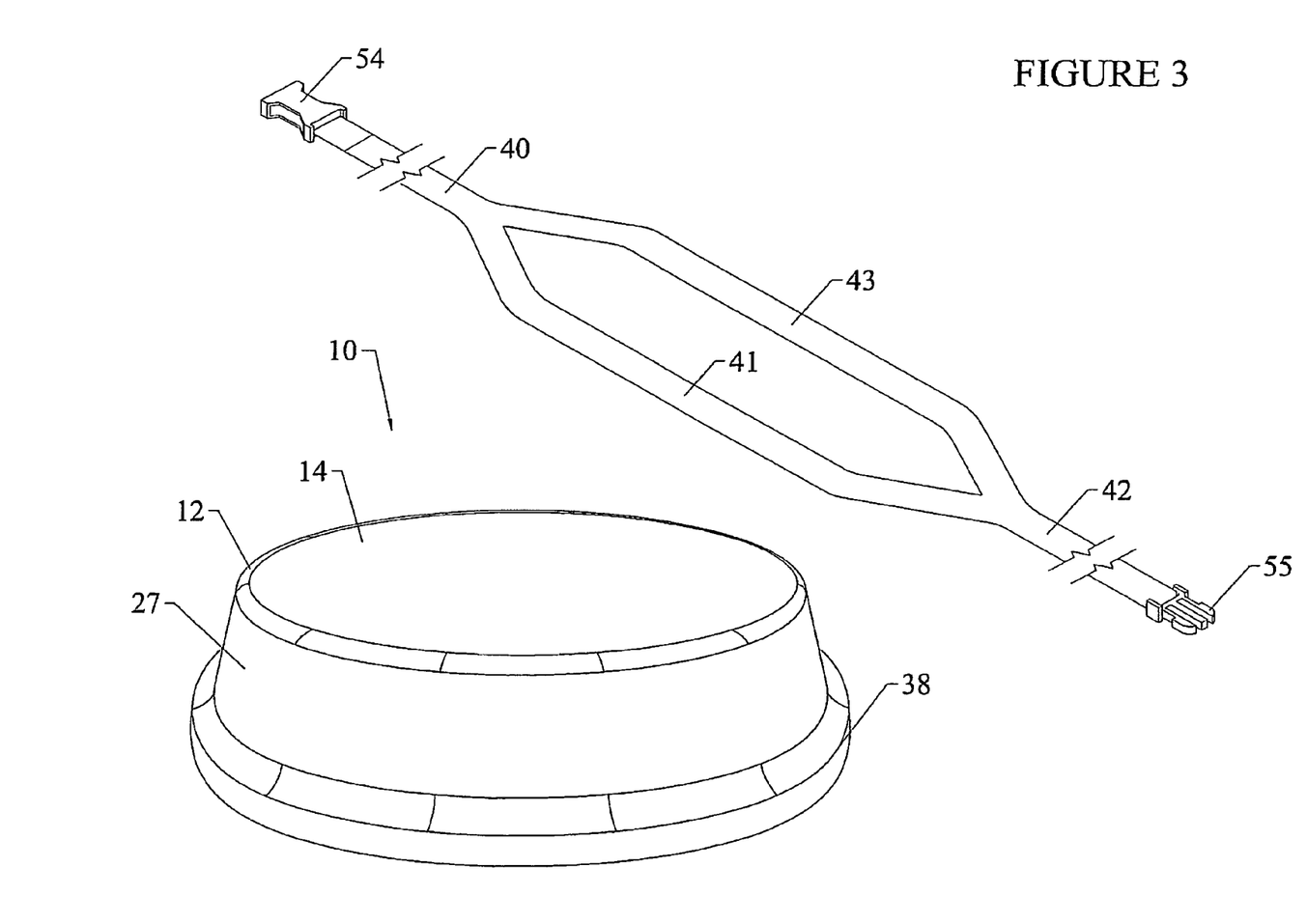
FIG. 3 depicts a perspective view of the outside surface of a flexible protective cover having a round one-piece flexible cover body.

Referring now to FIG. 3, a perspective view of an embodiment of the flexible protective cover having a round one-piece flexible cover body (10) with a central portion (12) having outside surface (14) is shown.

Central portion (12) has an edge (27) connected substantially perpendicular to central portion (12). Edge (27) can also be connected to central portion (12) at an angle. It is also contemplated that portions of edge (27) could be connected substantially perpendicularly to central portion (12), while other portions of edge (27) can be connected to central portion (12) at an angle.

Sealing member (38), which is depicted as flexible deformation resistant rubber, is shown disposed directly to edge (27) opposite central portion (12). In this depicted embodiment, it is contemplated that edge (27) can be made from a shapeable, bendable material, and central portion (12) can be made from a thin, shapeable material, such as a flexible plastic, rubber, or silicone barrier.

FIG. 3 further depicts a first adjustable strap (40) is shown engaging a first fastening strap (41) and a second fastening strap (43). A second adjustable strap (42) is shown engaging the opposite ends of first fastening strap (41) and second fastening strap (43).

It is contemplated that first adjustable strap (40) and second adjustable strap (42) are used to secure the flexible protective cover over an open epidermal site, while first fastening strap (41) and second fastening strap (43) apply pressure to the outside surface (14) of one-piece flexible cover body (10) to create a seal between sealing member (38) and the open epidermal site.

First adjustable strap (40) is shown having a first buckle (54), and second adjustable strap (42) is shown having means for engaging the first buckle (55). While FIG. 3 depicts a single buckle, any number of buckles or other types of hook and loop fasteners, slidable fastening means, or elastic straps can be used.

Figure 4:
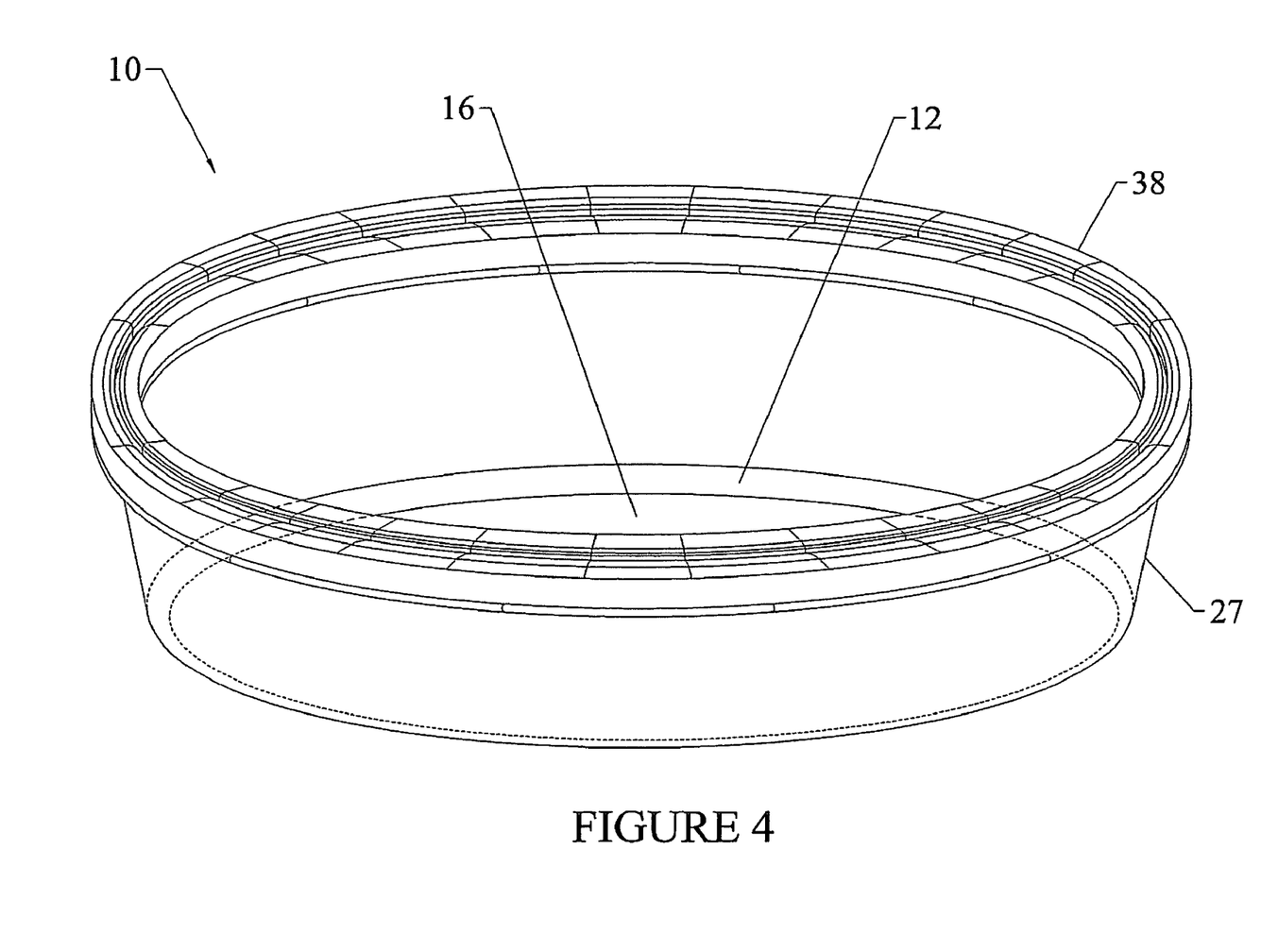
FIG. 4 depicts a perspective view of the inside surface of the flexible protective cover of FIG. 3.

Referring now to FIG. 4, a perspective view of the inside surface (16) of the flexible protective cover depicted in FIG. 3 is shown.

FIG. 4 depicts a round one-piece flexible cover body (10) having central portion (12) with inside surface (16). Edge (27) is connected substantially perpendicular to central portion (12). Sealing member (38) is disposed on edge (27). FIG. 4 depicts sealing member (38) as flexible, deformation resistant rubber, however, other types of sealing members, such as plastic-coated metal, inflatable tubing, deformation resistant tubing, and similar plastic, rubber, polymer, or other materials able to form a fluid-tight seal on a user are also contemplated.

Figure 5:
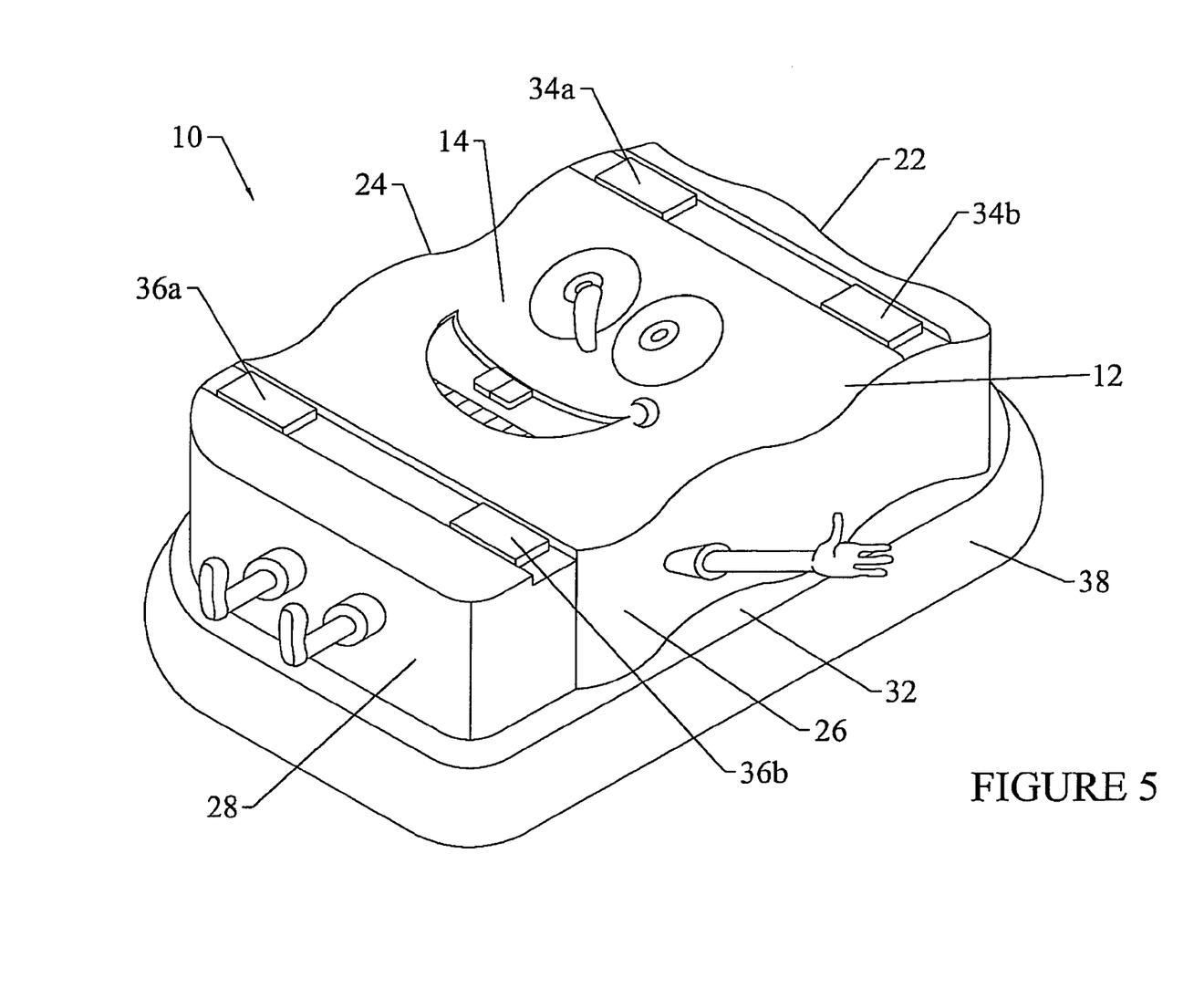
FIG. 5 depicts a perspective view of the outside surface of a flexible protective cover having a cartoon-shaped one-piece flexible cover body.

Referring now to FIG. 5, a perspective view of an embodiment of the flexible protective cover having a cartoon-shaped one-piece flexible cover body (10) with a central portion (12) having outside surface (14) is shown.

The cartoon-shaped one-piece flexible cover body (10) has a top edge (22), a first side edge (24), a second side edge (26), and an angular edge (28), which encircle the perimeter of the central portion (12) and are connected substantially perpendicular to central portion (12). Depending on the shape of the cartoon-shaped one-piece flexible cover body (10), fewer than four edges can be used, such as a triangular shaped or round one-piece flexible cover body.

A lip (32) is disposed over top edge (22), first side edge (24), second side edge (26), and angular edge (28). Sealing member (38) is shown disposed over lip (32).

A first anchored portion (34a) and a second anchored portion (34b) of a first fastener, and a first anchored portion (36a) and a second anchored portion (36b) of a second fastener are shown disposed on outside surface (14), for receiving complementary fastener portions attached to adjustable straps.

Figure 6:
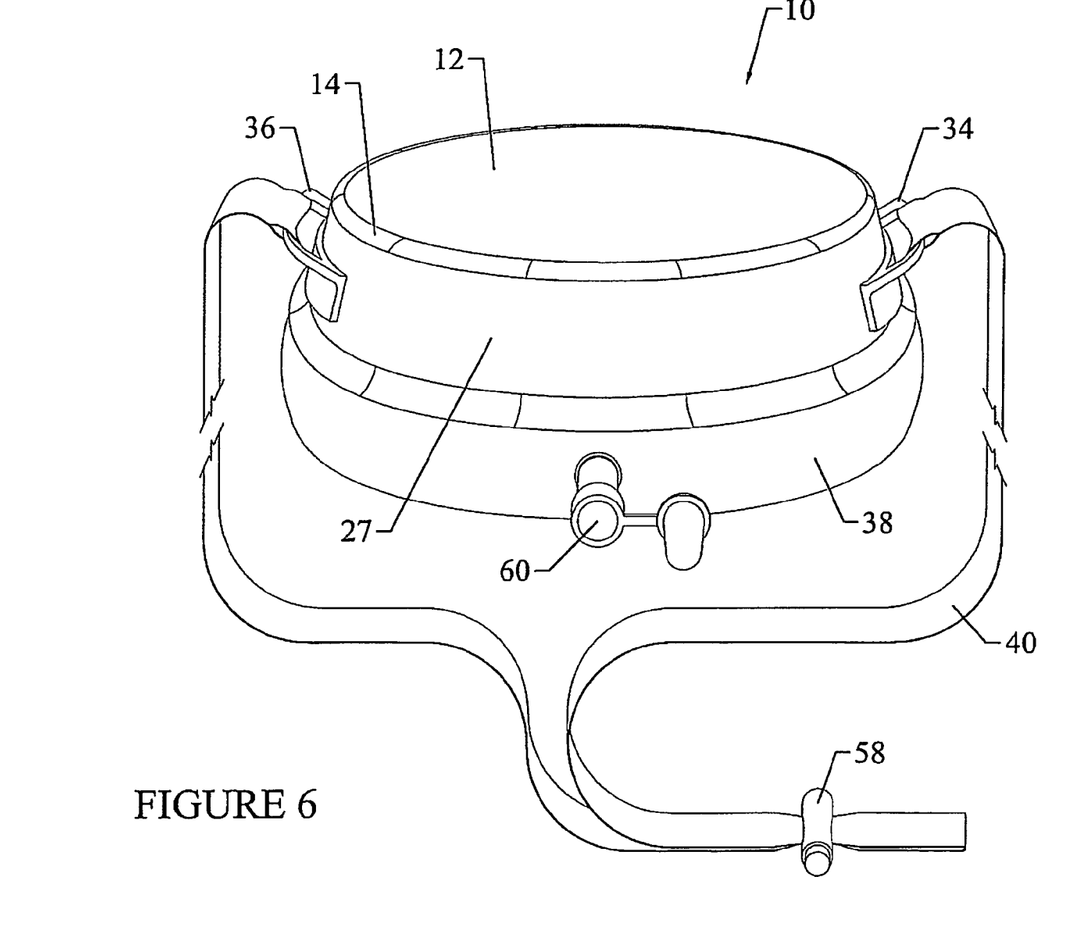
FIG. 6 depicts a perspective view of the outside surface of an alternative embodiment of the present flexible protective cover.

Referring now to FIG. 6, a perspective view of an alternative embodiment of the flexible protective cover is depicted. FIG. 6 further depicts an embodied flexible protective cover has a one-piece flexible cover body (10) having a central portion (12) with an outside surface (14).

Central portion (12) has an edge (27) connected substantially perpendicular to central portion (12). A sealing member (38), is depicted disposed on edge (27). Sealing member (38) is depicted as inflatable tubing having a valve (60), however sealing member (38) can also include other sealing members, such as deformation-resistant tubing, and similar plastic, rubber, polymer, or other materials able to form a fluid-tight seal on a user. It is contemplated that valve (60) can be any type of valve, including a removable valve or a non-removable valve.

A first fastener (34) and a second fastener (36) are depicted integral with the central portion (12). While first fastener (34) and second fastener (36) are depicted as plastic loops molded to the central portion (12), other types of fasteners, such as hook and loop fasteners, reusable adhesive, and other similar fasteners are also contemplated.

A first adjustable strap (40) is shown engaging first fastener (34) and second fastener (36). First adjustable strap (40) is contemplated to be an elastic material, however first adjustable strap (40) can also be a webbed material, a textile, a hypoallergenic material, or other similar materials.

A slidable fastener (58) is shown engaging first adjustable strap (40). It is contemplated that slidable fastener (58) can selectively engage and release first adjustable strap (40), such as through use of a switch or spring-actuated button, allowing slidable fastener (58) to move along first adjustable strap (40).

The movement of slidable fastener (58) allows first adjustable strap (40) to be tightened to cinch one-piece flexible cover body (10) to a user, forming a sealing engagement between sealing member (38) and an open epidermal site. Slidable fastener (58) can also be moved to loosen first adjustable strap (40) to allow removal of the flexible protective cover.

Figure 7:
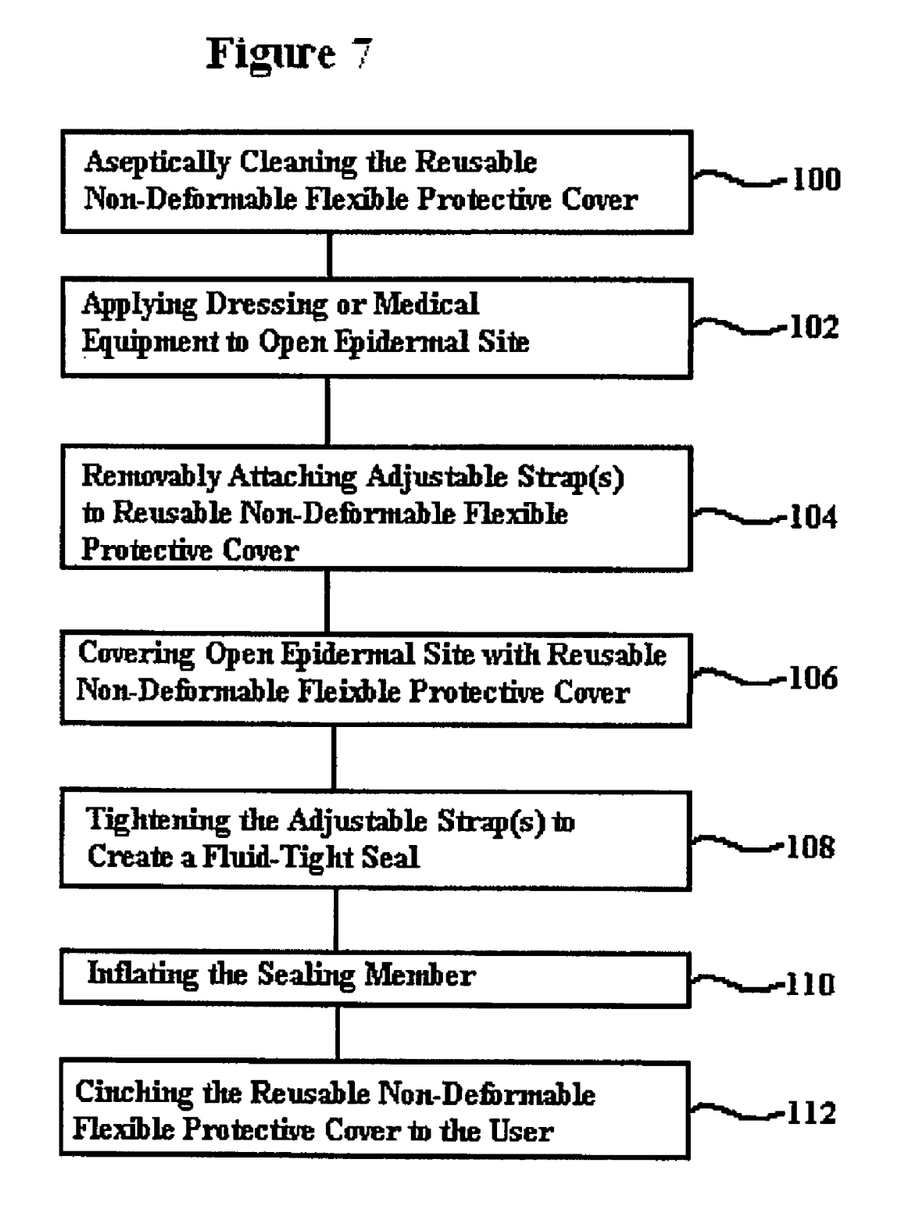
FIG. 7 is a diagram depicting the steps of an embodiment of the present method.

FIG. 7 depicts a diagram depicting the steps of an embodiment of the present method is shown.

The depicted embodiment includes aseptically cleaning a reusable non-deformable flexible protective cover (100). Aseptically cleaning the flexible protective cover can include washing or wiping the flexible protective cover with antibacterial and antiviral substances, which can be done manually or using mechanical washing machines. The step of aseptically cleaning the flexible protective cover can also include sterilizing the flexible protective cover, such as by using an autoclave. It is also contemplated that the flexible protective cover can be produced using sterile conditions and provided using sterile packaging materials, allowing this step to be omitted.

The depicted embodiment further includes applying a dressing or medical equipment to an open epidermal site (102). Dressings or medical equipment can include bandages, gauze, sutures, intravenous lines, central lines, Port-A-Caths™, catheters, other similar dressing means or medical equipment, and combinations thereof. In an embodiment, the flexible protective cover can be placed over an open epidermal site without a dressing, and this step can be omitted.

The depicted embodiment also includes removably attaching one or more adjustable straps to the flexible protective cover (104). This can be done using fasteners, such as Velcro™, snaps, reusable adhesive, magnets, or similar fastening means. Use of fasteners can also be omitted, and the straps can be secured directly to the outside surface of the flexible cover, such as by placement within grooves on the outside surface.

The open epidermal site is then covered with the flexible protective cover (106). It is contemplated that the flexible protective cover can be any size or shape necessary to accommodate open epidermal sites of any size or shape and dressings of any size or shape. In an embodiment, tubing or other medical equipment connected to the open epidermal site can be securely engaged with the flexible protective cover, such as by engaging the medical equipment, in a force fit, with one or more openings in an edge of the flexible protective cover, with one or more slits in an interior spacer within the flexible protective cover, or combinations thereof.

The adjustable straps can then be tightened, creating a fluid tight seal between the flexible protective cover and the open epidermal site (108). This can be done using buckles, slidable fasteners, or similar tightening means on the adjustable straps. It is also contemplated that the straps can be made from an elastic material that tightens around a user, eliminating the need for manually tightening the straps.

The depicted embodiment includes the optional step of inflating the sealing member of the flexible protective cover (110), such as by using a valve and a pump for providing air through the valve. This step can be performed to seal gaps between the flexible protective cover and the open epidermal site. It is also contemplated that the sealing member of the flexible protective cover can include a non-inflatable sealing member, and this step can be omitted.

The depicted embodiment concludes with the step of cinching the flexible protective cover to the user (112), which can include using buckles or other similar fastening means to securely tighten the flexible protective cover to a user. Cinching the flexible protective cover to the user prevents unintended motion of the flexible protective cover, which can destroy the seal.

While these embodiments have been described with emphasis on the embodiments, it should be understood that within the scope of the appended claims, the embodiments might be practiced other than as specifically described herein.

What is claimed is:

1. A method for preventing infection and maintaining aseptic epidermal areas by preventing contaminated fluid from entering an open epidermal site on a user, comprising the steps of:
   a. removably securing at least two adjustable straps to a reusable non-deforming flexible protective cover without the need for the use of adhesives comprising a sealing member, wherein the adjustable straps are secured over non-deforming flexible protective cover;
   b. covering the open epidermal site with the reusable non-deforming flexible protective cover while maintaining a space between the reusable non-deforming flexible protective cover and the open epidermal site; and
   c. tightening the at least two adjustable straps to secure the reusable non-deforming flexible protective cover over the open epidermal site and apply pressure to the reusable non-deforming flexible protective cover to create a fluid-tight seal around the open epidermal site, thereby preventing contaminated fluid from entering the open epidermal site.

2. The method of claim 1, wherein the reusable non-deforming flexible protective cover further comprises:
   a. a one-piece flexible cover body for covering the open epidermal site, wherein the one-piece flexible cover body comprises:
      i. a central portion having an outside surface and an inside surface;
      ii. at least one edge connected to the central portion at an angle; and
      iii. a lip disposed around the edge;
   b. a sealing member disposed over the lip for providing a sealing engagement between the lip and the open epidermal site and preventing fluid from entering the open epidermal site; and
   c. at least two adjustable straps removably connected to the outside surface, wherein the at least two adjustable straps secure the one-piece flexible cover body over the open epidermal site, applies pressure to the one-piece flexible cover body forming the sealing engagement, and secures the one-piece flexible cover body to the user.

3. The method of claim 1, wherein the wherein the reusable non-deforming flexible protective cover further comprises:
   a. a one-piece flexible cover body for covering the open epidermal site, wherein the one-piece flexible cover body comprises:
      i. a central portion having an outside surface and an inside surface; and
      ii. at least one edge connected to the central portion at an angle;
   b. an inflatable sealing member integral with the edge and providing a sealing engagement between the one-piece flexible cover body and the open epidermal site for preventing fluid from entering the open epidermal site; and
   c. at least one adjustable strap removably connected to the outside surface, wherein the at least one adjustable strap secures the one-piece flexible cover body over the open epidermal site, applies pressure to the one-piece flexible cover body forming the sealing engagement, and secures the one-piece flexible cover body to the user.

4. The method of claim 1, further comprising the step of applying at least one dressing means to the open epidermal site.

5. The method of claim 4, wherein the dressing means is selected from the group consisting of: a bandage, gauze, a catheter, an intravenous line, a peripheral intravenous line, a port for central venous access, a central venous line, a catheter line, at least one suture, or combinations thereof.

6. The method of claim 1, further comprising the step of securely engaging tubing connected to the open epidermal site with at least one opening in the reusable non-deforming flexible protective cover.

7. The method of claim 1, wherein the step of removably attaching at least two adjustable straps comprises fastening each of the at least two adjustable straps to at least one fastener having an anchored portion disposed on the reusable non-deforming flexible protective cover, at least one fastener integral with the outside surface of the reusable non-deforming flexible protective cover.

8. The method of claim 1, wherein the sealing member is an inflatable sealing member, the method further comprising the step of inflating the inflatable sealing member to seal gaps between the reusable non-deforming flexible protective cover and the open epidermal site.

9. The method of claim 1, further comprising the step of cinching the reusable non-deforming flexible protective cover to the user using at least one buckle connected to one of the at least two adjustable straps, at least one slidable fastener connected to the one of the adjustable straps, or combinations thereof.

10. The method of claim 1, further comprising the step of aseptically cleaning the reusable non-deforming flexible protective cover.

* * * * *